US00PP36124P3

(12) United States Plant Patent
Schoone

(10) Patent No.: US PP36,124 P3
(45) Date of Patent: Sep. 17, 2024

(54) ***PHALAENOPSIS* PLANT NAMED 'Cloud Busters'**

(50) Latin Name: *Phalaenopsis hybrida*
Varietal Denomination: Cloud Busters

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 18/527,339

(22) Filed: Dec. 3, 2023

(65) Prior Publication Data

US 2024/0188466 P1 Jun. 6, 2024

Related U.S. Application Data

(60) Provisional application No. 63/430,035, filed on Dec. 4, 2022.

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 5/02; A01H 5/00; A01H 6/62
See application file for complete search history.

*Primary Examiner* — June Hwu
(74) *Attorney, Agent, or Firm* — C. Anne Whealy

(57) ABSTRACT

A new and distinct cultivar of *Phalaenopsis* plant named 'Cloud Busters', characterized by its relatively compact and upright plant habit; moderately vigorous to vigorous growth habit; strong flowering stems; strong leaves; freely flowering habit with typically four inflorescences developing per plant, each inflorescence with numerous flowers; flowers with white-colored petals and sepals; flowers with white and yellow-colored labella; and good postproduction longevity.

2 Drawing Sheets

CROSS-REFERENCED TO CLOSELY-RELATED APPLICATIONS

Figure 1:
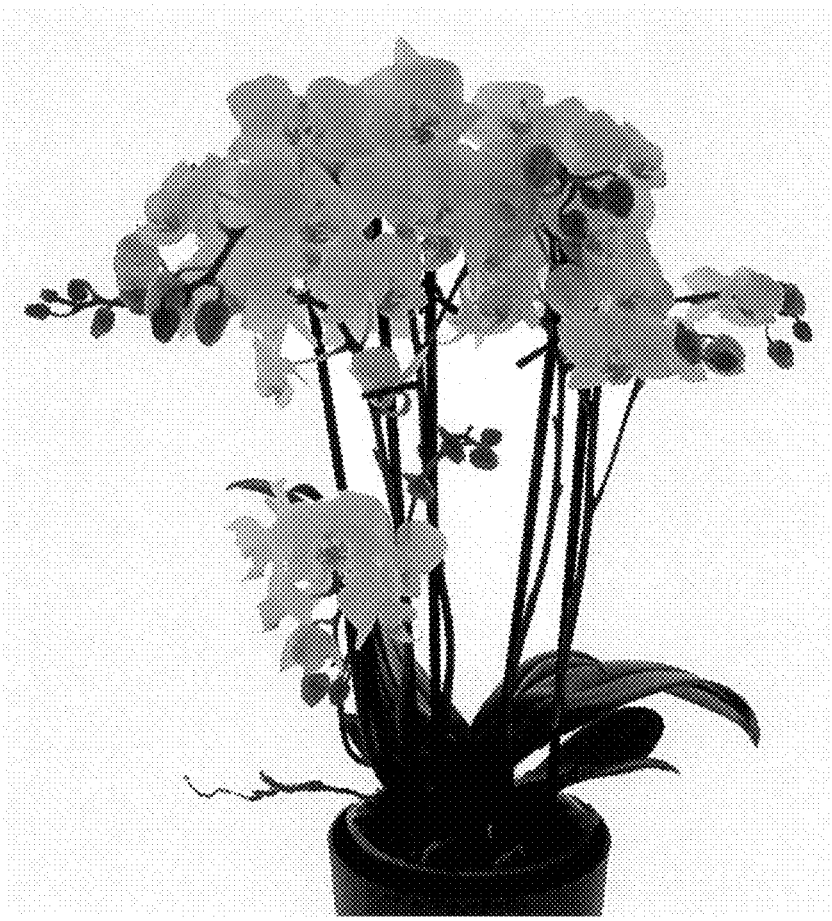

Title: Varieties of *Phalaenopsis* Plants
Inventor: René Schoone
Filed: Dec. 4, 2022
Ser. No.: 63/430,035
Inventor and Applicant/Assignee hereby claims the benefit of this provisional U.S. Patent Application.
Botanical designation: *Phalaenopsis hybrida.*
Cultivar denomination: 'CLOUD BUSTERS'.

STATEMENT REGARDING PRIOR DISCLOSURES BY INVENTOR AND APPLICANT/ASSIGNEE

An European Community Plant Breeder's Rights application for the instant plant was filed by the Applicant/Assignee of the instant application, Floricultura B.V. of Heemskerk, The Netherlands on Dec. 20, 2022, application number 2022/3096. Foreign priority is not claimed to this application.

The Inventor and Applicant/Assignee assert that no sales, offers for sale or public distribution of the instant plant occurred more than one year prior to the effective filing date of this application.

Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosures and/or sales prior to the filing date but less than one year prior to the effective filing date.

BACKGROUND OF THE INVENTION

The present invention relates to a new and distinct cultivar of *Phalaenopsis* plant, botanically known as *Phalaenopsis hybrida*, and hereinafter referred to by the name 'Cloud Busters'.

The new *Phalaenopsis* plant is a product of a planned breeding program conducted by the Inventor in Nantou, Taiwan; Heemskerk, The Netherlands; and Assendelft, The Netherlands. The objective of the breeding program is to develop new fast-growing and freely flowering *Phalaenopsis* plants with good leaf shape and flowers with unique and attractive patterns and coloration.

The new *Phalaenopsis* plant originated from a cross-pollination in September, 2014 in Nantou, Taiwan of *Phalaenopsis hybrida* 'Timothy Christopher' x 'Cassandra', not patented, as the female, or seed, parent with *Phalaenopsis hybrida* 'Amabilis', not patented, as the male, or pollen, parent. The new *Phalaenopsis* plant was discovered and selected by the Inventor as a single flowering plant from within the progeny of the stated cross-pollination grown in a controlled greenhouse environment in Heemskerk, The Netherlands in October, 2018.

Asexual reproduction of the new *Phalaenopsis* plant by in vitro meristem propagation in a controlled environment in Assendelft, The Netherlands since October, 2019 has shown that the unique features of this new *Phalaenopsis* plant are stable and reproduced true to type in successive generations.

SUMMARY OF THE INVENTION

Plants of the new *Phalaenopsis* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Cloud Busters'. These characteristics in combination distinguish 'Cloud Busters' as a new and distinct *Phalaenopsis* plant:

1. Relatively compact and upright plant habit.
2. Moderately vigorous to vigorous growth habit.
3. Strong flowering stems.
4. Strong leaves.
5. Freely flowering habit with typically four inflorescences developing per plant, each inflorescence with numerous flowers.
6. Flowers with white-colored petals and sepals.
7. Flowers with white and yellow-colored labella.
8. Good postproduction longevity.

Plants of the new *Phalaenopsis* can be compared to plants of the female parent, 'Timothy Christopher' x 'Cassandra'. Plants of the new *Phalaenopsis* differ primarily from plants of 'Timothy Christopher' x 'Cassandra' in the following characteristics:

1. Flower petals of plants of the new *Phalaenopsis* are close to imbricate whereas flower petals of plants of 'Timothy Christopher' x 'Cassandra' are not imbricate.
2. Labella of the plants of the new *Phalaenopsis* are white and yellow in color whereas flower sepals of plants of 'Timothy Christopher' x 'Cassandra' are mostly white in color with a small soft yellow-colored area.

Plants of the new *Phalaenopsis* can be compared to plants of the male parent, 'Amabilis'. Plants of the new Phalaenopsis differ primarily from plants of 'Amabilis' in the following characteristics:

1. Flower petals of plants of the new *Phalaenopsis* are close to imbricate whereas flower petals of plants of 'Amabilis' are not imbricate.
2. Labella of the plants of the new *Phalaenopsis* are white and yellow in color whereas labella of plants of 'Amabilis' are mostly white in color with a small soft yellowish green-colored area.

Plants of the new *Phalaenopsis* can be compared to plants of *Phalaenopsis hybrida* 'Soft Cloud', not patented. In side-by-side comparisons, plants of the new *Phalaenopsis* differ primarily from plants of 'Soft Cloud' in the following characteristics:

1. Leaves of plants of the new *Phalaenopsis* are semi-erect to horizontal in aspect whereas leaves of plants of 'Soft Cloud' are drooping.
2. Plants of the new *Phalaenopsis* are not as freely flowering as plants of 'Soft Cloud'.
3. Peduncles of the plants of the new *Phalaenopsis* are not tinged with anthocyanin whereas peduncles of plants of 'Soft Cloud' are strongly tinged with anthocyanin.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'Cloud Busters' grown in a container.

Figure 2:
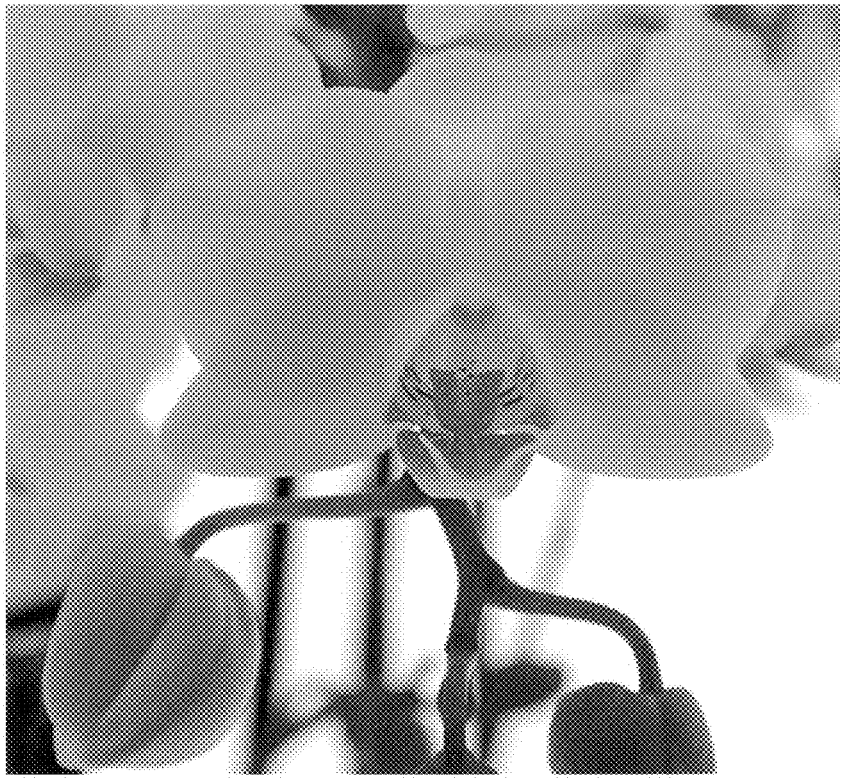

The photograph on the second sheet (FIG. 2) is a close-up view of typical flower buds and a typical flower of 'Cloud Busters'.

DETAILED BOTANICAL DESCRIPTION

The aforementioned photographs and following observations and measurements describe plants grown during the early spring in 10.5-cm containers in a glass-covered greenhouse in Heemskerk, The Netherlands and under cultural practices typically used in commercial *Phalaenopsis* production. Plants were 18 months old when the photographs and description were taken. During the first twelve months of production of the plants, day and night temperatures averaged 27C. During the final six months of production of the plants, day temperatures ranged from 20C to 22C and night temperatures ranged from 18C to 20C. During the production of the plants, light levels ranged from a minimum of 5,000 lux to a maximum of 10,000 lux. In the following description, color references are made to The Royal Horticultural Society Colour Chart, 2015 Edition, except where general terms of ordinary dictionary significance are used.

Botanical classification: *Phalaenopsis hybrida* 'Cloud Busters'.

Parentage:

*Female, or seed, parent.*—*Phalaenopsis hybrida* 'Timothy Christopher' x 'Cassandra', not patented.

*Male, or pollen, parent.*—*Phalaenopsis hybrida* 'Amabilis', not patented.

Propagation:

*Type.*—By in vitro meristem propagation.

*Time to initiate roots, summer and winter.*—About two weeks at temperatures about 28C to 30C.

*Time to produce a rooted young plant, summer and winter.*—About 20to 25 weeks at temperatures about 28C to 30C.

*Root description.*—Thin, fibrous; typically light yellowish white in color; actual color of the roots is dependent on substrate composition, water quality, fertilizer, substrate temperature and age of roots.

*Rooting habit.*—Freely branching; medium density.

Plant description:

*Plant form and growth habit.*—Herbaceous epiphyte; upright plant habit with typically four inflorescences developing per plant, each inflorescence with numerous flowers; monopodial; moderately vigorous to vigorous growth habit and moderate growth rate.

*Plant height, substrate level to top of foliar plane.*—About 15 cm.

*Plant height, substrate level to top of floral plane.*—About 31.5 cm.

*Plant diameter or spread.*—About 27.7 cm.

Leaf description:

*Arrangement and quantity.*—Distichous, simple; sessile; about five leaves per plant.

*Length.*—About 18.4 cm.

*Width.*—About 6.4 cm.

*Aspect.*—Semi-erect to horizontal and eventally outwardly arching.

*Shape*.—Narrowly obovate to elliptic-oblong; slightly carinate.

*Apex*.—Unequal acute to unequal broadly acute.

*Base*.—Sheathing. Sheath length: About 1.5 cm. Sheath width: About 1.3 cm. Sheath color: Close to 143A.

*Margin*.—Entire; not undulate.

*Texture and luster, upper and lower surfaces*.—Smooth, glabrous; slightly glossy.

*Venation pattern*.—Camptodromous.

*Color*.—Developing and fully expanded leaves, upper surface: Close to a blend of 143A and 146A; venation, close to 147A. Developing and fully expanded leaves, lower surface: Close to a blend of 146A and 146B; venation, close to 144A.

Inflorescence description:

*Appearance and flowering habit*.—Showy zygomorphic flowers arranged on axillary simple or branched racemes; typically four inflorescences develop per plant; each inflorescence with about 25flowers; flowers face outwardly on outwardly arching inflorescences supported by upright peduncles; flowers with three petals, two lateral petals and one center petal transformed into a labellum and three sepals.

*Fragrance*.—None detected.

*Time to flower*.—Plants begin flowering about five months after planting; plants flower naturally during the winter into the spring.

*Flower longevity*.—Long flowering period, individual flowers maintain good substance for about eight weeks on the plant; flowers not persistent.

*Inflorescence length* (*lowermost flower to inflorescence apex*).—About 27 cm.

*Inflorescence width*.—About 13.9 cm.

*Flower buds*.—Height: About 1.5 cm. Diameter: About 1.1 cm by 1.3 cm. Shape: Broadly ovate. Color: Close to 145C.

*Flower size*.—About 4.6 cm (vertical) by 5.2 cm (horizontal).

*Flower depth*.—About 2.5 cm.

*Petals, quantity and arrangement*.—Three, two lateral petals and one center petal transformed into a labellum.

*Lateral petals*.—Length: About 2.5 cm. Width: About 2.7 cm. Shape: Reniform to roughly deltoid. Apex: Broadly obtuse. Margin: Entire; not undulate. Texture and luster, upper and lower surfaces: Smooth, glabrous, velvety; matte. Color: When opening, upper surface: Close to 157D; towards the margins and apex, close to 155C. When opening, lower surface: Close to 157B; towards the margins and apex, close to 157D. Fully opened, upper and lower surfaces: Close to NN155D; color does not change with subsequent development.

*Labella*.—Appearance: Three-parted with two lateral lobes and a central lobe. Length, lateral lobes: About 1.5 cm. Width, lateral lobes: About 1 cm. Length, central lobe: About 1.4 cm. Width, central lobe: About 4 mm to 12 mm. Length, cirrhose tips: About 7 mm. Shape, lateral lobes: Ovate. Shape, central lobe: Narrowly deltoid. Apex, lateral lobes: Obtuse. Apex, central lobe: Cleft with two reflexed cirrhose apices. Margins, lateral and central lobes: Entire. Texture and luster, lateral and central lobes, upper and lower surfaces: Smooth, glabrous, moderately velvety; matte. Callosities: Located at the base of the labellum and attachment point of the lateral petals; about 3 mm in length, about 4 mm in width and about 4 mm in height. Color: When opening, upper surface: Lateral lobes: Close to NN155D; proximal margins, close to 8A; at the base, sparse dots and stripes, close to 174A. Central lobe: Close to 22A and 22B; towards the apex, close to 8B and apices, close to NN155C; cirrhose tips, close to NN155C; at the base, close to NN155C; radial stripes, close to 174A. Callosities: Close to 11A and 11B; fine dots, close to 174B. When opening, lower surface: Lateral lobes: Close to NN155C; proximal margins, close to 8A. Central lobe: Close to 155C; towards the base, close to 11A and at the base, close to 155B; cirrhose tips, close to 155C. Fully opened, upper surface: Lateral lobes: Close to NN155D; proximal margins, close to 11A; at the base, sparse dots and stripes, close to 174A and 174B. Central lobe: Close to 22C and 22D; towards the apex, close to NN155D; cirrhose tips, close to NN155D; at the base, close to NN155C; radial stripes, close to 174A to 174B. Callosities: Close to 11A and 11B; fine dots, close to 174B. Fully opened, lower surface: Lateral lobes: Close to NN155C; proximal margins, close to 11A. Central lobe: Close to NN155C; towards the base, close to 11B and at the base, close to 155B; cirrhose tips, close to NN155C.

*Sepals*.—Quantity and arrangement: Three, one upper dorsal sepal and two lower lateral sepals. Length, dorsal sepal: About 2.6 cm. Width, dorsal sepal: About 1.6 cm. Length, lateral sepals: About 2.6 cm. Width, lateral sepals: About 1.7 cm. Shape, dorsal and lateral sepals: Ovate. Apex, dorsal sepal: Bluntly acute. Apex, lateral sepals: Acute. Base, dorsal and lateral sepals: Truncate. Margins, dorsal and lateral sepals: Entire; not undulate. Texture and luster, dorsal and lateral sepals, upper and lower surfaces: Smooth, glabrous, moderately velvety; matte. Color, dorsal sepal: When opening, upper surface: Close to 155C. When opening, lower surface: Close to 145D; towards the margins and apex, close to 157A. Fully opened, upper and lower surfaces: Close to NN155D; color does not change with subsequent development. Color, lateral sepals: When opening, upper surface: Close to 155C; towards the base, close to 145D; at the base, fine dots, close to 174A and 174B. When opening, lower surface: Close to 157A; towards the base, close to 145C and 145D. Fully opened, upper and lower surfaces: Close to NN155D; color does not change with subsequent development.

*Penduncles*.—Length: About 37.9 cm. Diameter: About 4 mm. Strength: Strong. Aspect: Upright to outwardly arching. Texture and luster: Smooth, glabrous; matte. Color: Close to 143B.

*Pedicels*.—Length: About 3.6 cm. Diameter: About 2 mm. Strength: Moderately strong. Aspect: About 80 degrees from peduncle axis. Texture and luster: Smooth, glabrous; matte. Color: Close to 145D; proximally, close to 144A and 144B.

*Reproductive organs*.—Androecium: Column length: About 7 mm. Column width: About 4 mm. Column color: Close to NN155C. Pollinia quantity: Two. Pollinia diameter (per two pollinia): About 2 mm. Pollinia color: Close to 23B. Gynoecium: Stigma length: About 4 mm. Stigma width: About 3 mm. Stigma shape: Reniform. Stigma color: Close to N155A. Ovary length: About 5 mm. Ovary diameter: About 0.75 mm. Ovary color: Close to N144D. Seeds and fruits: To date, seed and fruit development have not been observed on plants of the new *Phalaenopsis*.

Pathogen & pest resistance:

To date, plants of the new *Phalaenopsis* have not been shown to be resistant to pathogens and pests common to *Phalaenopsis* plants.

Temperature tolerance:

Plants of the new *Phalaenopsis* have been observed to tolerate high temperatures about 40C and are suitable for USDA Hardiness Zones 10 to 12.

It is Claimed:

1. A new and distinct *Phalaenopsis* plant named 'Cloud Busters' as illustrated and described.

* * * * *